United States Patent
Gafsou

(10) Patent No.: US 10,379,092 B2
(45) Date of Patent: Aug. 13, 2019

(54) SYSTEM AND METHOD FOR SCENT PERCEPTION MEASUREMENTS AND FOR CONSTRUCTION OF A SCENT DATABASE

(71) Applicant: Alon Daniel Gafsou, Rishon Lezion (IL)

(72) Inventor: Alon Daniel Gafsou, Rishon Lezion (IL)

( * ) Notice: Subject to any disclaimer, the term of this patent is extended or adjusted under 35 U.S.C. 154(b) by 816 days.

(21) Appl. No.: 14/892,137

(22) PCT Filed: May 20, 2014

(86) PCT No.: PCT/IL2014/050444
§ 371 (c)(1),
(2) Date: Nov. 18, 2015

(87) PCT Pub. No.: WO2014/188419
PCT Pub. Date: Nov. 27, 2014

(65) Prior Publication Data
US 2016/0091470 A1 Mar. 31, 2016

Related U.S. Application Data
(60) Provisional application No. 61/825,535, filed on May 21, 2013.

(51) Int. Cl.
*G01N 33/00* (2006.01)
(52) U.S. Cl.
CPC ..... *G01N 33/0001* (2013.01); *G01N 33/0034* (2013.01)
(58) Field of Classification Search
CPC ............ G01N 33/0001; G01N 33/0034
USPC .......................................................... 702/22
See application file for complete search history.

(56) References Cited

U.S. PATENT DOCUMENTS

| 5,627,307 | A  | 5/1997  | Hayashi         |
| 6,496,742 | B1 | 12/2002 | Labreche et al. |
| 6,496,813 | B1 | 12/2002 | Labreche et al. |
| 7,167,815 | B2 | 1/2007  | Labreche et al. |

(Continued)

FOREIGN PATENT DOCUMENTS

WO   WO2006/059815   6/2006

OTHER PUBLICATIONS

International Search Report and Written Opinion from International Application No. PCT/IL2014/050444 dated Sep. 23, 2014.

*Primary Examiner* — Anthony Ho
(74) *Attorney, Agent, or Firm* — Dorsey & Whitney LLP

(57) ABSTRACT

An electronic sensing unit is used to receive an odorant sample and generate an electronic signature characterizing the sample received therein via a guiding unit that guides a first portion of the sample into an electronic sampling unit and a second portion of the sample towards an outlet. A control unit is used to receive data indicative of the signature generated by the sensing unit and data from user(s) indicative of olfactive descriptors characterizing the sample to which the users are exposed, thereby enabling creation of a data record including first and second characterizing data corresponding to the same sample. The database includes such data records, each being associated with a specific odorant sample, which may then be used to characterise, formulate, and/or create, a desired scent based on comparison of an electric signature generated for the scent and data records which signatures comply with some best compliance criterion.

30 Claims, 5 Drawing Sheets

(56) References Cited

U.S. PATENT DOCUMENTS

| | | |
|---|---|---|
| 7,593,863 B1 | 9/2009 | Sunshine et al. |
| 7,734,436 B2 | 6/2010 | Labreche et al. |
| 8,272,280 B2 | 9/2012 | Jones, Jr. |
| 2012/0143804 A1 | 6/2012 | Haddad et al. |

SYSTEM AND METHOD FOR SCENT PERCEPTION MEASUREMENTS AND FOR CONSTRUCTION OF A SCENT DATABASE

TECHNOLOGICAL FIELD

The present invention is in the field of odor perception analysis and identification.

BACKGROUND

Over the last decade, "electronic sensing" technologies have undergone important developments from a technical and commercial point of view. The expression "electronic sensing" refers to the capability of reproducing human senses using sensor arrays and pattern recognition systems. Since 1982 research has been conducted to develop technologies, commonly referred to as electronic noses that could detect and recognize odors and flavors. These devices have undergone much development and are now used to fulfill industrial needs.

Electronic nose instruments are used by research and development laboratories, quality assurance (QA), quality control (QC) laboratories and process & production departments for various purposes: Many devices for detecting odors exist, all of which take into account the specific chemical composition of the volatile components of the sample a scent.

Some examples of devices known from the patent literature are briefly described below.

US Patent Publication No. 2012/0143804, the disclosure of which is incorporated here by reference, describes an apparatus for assessing odors by an electric nose, to be applied to an odor and to output a structure identifying the odor; a neural network which maps an extracted structure to a first location on a pre-learned axis of odor pleasantness; and an output for outputting an assessment of an applied odor based on said first location. The assessment may be a prediction of how pleasant a user will consider the odor.

U.S. Pat. No. 8,272,280 presents a method and apparatus for detecting contaminants in the food industry by collecting air samples by containing aerosolized contaminate particles from a foodstuff and analyzing the sample for presence of a contaminate. Aerosol lab-on-a-chip and/or electronic nose devices are utilized for the detection of contaminant particles.

U.S. Pat. No. 7,593,863 describes systems and methods for measuring and testing a product using artificial olfactometry and analytical data sensory to identify preferences, which accurately facilitates a consumer's choice between products using descriptors of similar yet different products. The systems and methods provide an objective recommendation based upon analytical descriptors and attributes of particular products, and eliminate the subjective recommendations of persons familiar with many comparable and related products and thereby makes objective recommendations between products.

U.S. Pat. No. 7,167,815 suggests quantifying the intensity of an odour by determining what is the response of an odour sensing device to that odour, then transforming the response data to an odour intensity value based on transformation data relating to a set of selected reference odours. The transformation data includes organoleptic data indicating how odour intensity values assigned to the set of reference odours by a sensory panel depend upon the concentration of the reference compounds and includes data indicating how the response data of the odour sensing device when exposed to the set of reference odours depends upon the concentration of the reference compounds. The reference odours may be basic odours defining the dimensions of a multi-dimensional space in which odours can be defined.

U.S. Pat. No. 5,627,307 describes an odor intensity index measuring apparatus for measuring odor intensity objectively and easily for various types of odor. Sample air is diluted with odorless air at a desired scale factor in a dilution unit. The diluted air is fed through an air duct to an odorometer. Corresponding to the intensity of odor, voltage V is emitted from the odorometer. In an electronic control unit, the scale factor at which sample air is diluted by the dilution unit is gradually increased. The dilution scale factor which is reached when the output voltage from the odorometer becomes lower than the specified value indicating the odorless condition is displayed on a liquid crystal display. Like the conventional three bag odor comparison method, the odor intensity index can be measured in the same manner for various types of odor. Different from the conventional method, the degree of the odor intensity can be measured objectively without relying on the human sense of smell.

U.S. Pat. No. 7,734,436 describes comparative analysis of a sample, derived from a product, with respect to a database by determining the class membership of the different characteristics (variables) describing the samples: are they characteristics common to the sample under test and the database, are they characteristics particular to the sample under test, or are they characteristics particular to the database? The assignment of the variables to these classes enables parameters to be defined for global comparison of the sample under test and the database, based on: ratios summarizing the values taken by the variables of the different classes, or the distribution of the variables of the different classes.

GENERAL DESCRIPTION

Odor measuring devices commercially available nowadays, like electronic nose and Gas Chromatograph systems, analyze smells according to their specific chemical composition, and not in a way that a human being perceives it.

The present invention generally relates to a system and method of constructing and using a database of scents (odors). Each record in the database associates a specific odor characteristics (or a specific group of odors) with an electronic signature obtained using an electronic nose (sensor) unit, a set of olfactive descriptors associated with the specific odor sample obtained from a biologic nose (e.g., one or more panellists), and a set of olfactive descriptors associated with the specific odor sample generated based on the electronic signature data. The data record associated with each specific odor is then used to forecast and define at least one olfactive descriptor, which may be then used to forecast and define at least one olfactive index, at least one olfactive perception (i.e., naming), and a final score, for the specific odor sample. The information in each database record may be referred to the naming of the specific odor/scent with several options e.g., Vanilla, Rose etc.

Typically systems utilizing an electronic nose are not designed to characterize olfactive descriptors of a smell, its value and its importance like humans, without pre-calibration of the device and assigning it to a specific object or situation. To date, all commercial devices are adapted to detect smells according to a chemical composition and not in a way that a human being (or any other living creature) percepts it. Therefore, these devices should be pre-calibrated to each specific case, the output in most cases should be analyzed by experts, and there are typically differences from one batch of the device to another. Due to the measuring process, e.g., requiring heating, some modifications of olfactive description and/or of the chemical composition may occur. In the existing electronic nose systems there is no mutual information change. In addition, perception relates to the experience and attention of people, to their health condition, hormonological conditions and such like. Thus, there is a long felt need for a device capable of detecting a smell in an objective way, and capable of assigning it to a certain perception.

Typically, conventional devices need to be pre calibrated to each specific case/application. Therefore there is a strong need for a global/generic system/device, in which each device is not required to be pre calibrated to each specific case/application enabling an endless construction of a database by kind of "crowed sourcing". In general, one of the main obstacles for achieving it is that the same sensor, from different batches, has slightly different sensitivity. In some embodiments of the present invention this problem is solved by using a pre calibrating unit, which may be part of the complete system, based on predefined references. In other words, for conventional devices, device A and device B having the same sensor, would have slightly different electronic signature, which in case of applying the same mathematical test, like pattern recognition, on both devices, may results in different identifications while in embodiments of the present invention, device A and device B would have the same identification therefore enabling a construction of a database from different devices as well. There is a need in the art for odor evaluation devices capable of sampling and analysing odorant materials and providing descriptors associated with the sampled odorant material and complying with human subjects' perception.

Thus, one aspect of the present invention concerns construction of a global scent perception database (also refereed to herein as olfactive or scent database) of odorant materials. The database may be prepared as follows: a specific odorant material (pure molecule or a mixture) or predefined set/group of odorant materials is/are sampled (i.e., gas phase sample(s) is/are prepared), and then tested by concurrently analyzing it by an electronic sensing unit and by a biologic nose (e.g., professional, or non-professional, human subject), and for each odorant sample (or group) respective electronic signature (data) is generated by the sensing unit and respective perception data is received from biologic nose. The perception data includes a number of descriptors (parameters), and additional sensorial properties (e.g., softness, perception of space) may be also obtained from the biologic nose. Thus, each electronic signature is stored with its associated set of values for the predetermined descriptor/s. The descriptors actually present classification data for the respective odorant sample, which enables its identification by the electronic signature stored in the database.

In general, each record in the database may comprise one or more of the following: record name, the different parameters in which the system is operating (for example, and without limiting, sensor's temperature, size of sample, concentration, humidity, velocity, pressure; and any combination thereof), sensor's activity data; instructions for building the descriptor's scale, data processing instructions, at least one olfactive descriptor, at least one olfactive index; at least one olfactive perception; indications concerning specific mental and/or psychological situations, and/or health diagnostic, and/or sensorial properties derivable based on the different descriptors (like for example illness stage); and any combination thereof.

The term "olfactive descriptor" or "scent descriptor" refers to data/parameter that describes scent characteristics e.g., Intensity, pleasantness, olfactive families such as defined by descriptors in Dravnieks atlas, for example, Fruity, Floral, etc. in the database records. Each olfactive descriptor has a certain value/score obtained from the biologic nose (e.g., one or more panelists) on an objective scale. More particularly, the term relates to the properties of a scent, technical or not, influencing and/or describing its perception such as: cognitive perception, behavioral, physico-chemical properties, psychological, psychophysical, organoleptic properties, pleasantness, repulsion, intensity, odor threshold, molecular weight, molecular size, molecular branching, molecular surface area, droplets size, the tendency to absorb liquids, ionization potential, "irritation" level, familiarity, blotter life, evaporation rate, vapor pressure, humidity of scent sample, temperature of scent sample, etc. It is noted that the term "olfactive descriptor" may refer mainly, to human perception, but may also refers to neural/brain activity (or behavioral response) of any living creature measured responsive to the presence of an odorant.

The term "biologic nose" refers to receptors/sensors of a leaving creature, such as, but not limited to, human nose, animal nose and to any leaving creature having a certain response to a volatile component, and any combination thereof.

The term "olfactive index" refers to quantifying scale of at least two olfactive descriptors and their values, typically determined in cases where there are more than one descriptor being associated with a specific odor sample. Olfactive indices may be any combination of two or more olfactive descriptors, and their respective grades, as obtained from the electronic or biologic nose in response to a specific odor sample. Optionally, and in some embodiments preferably, each olfactive index is generated in context of a specific application/consumer product applicable to the odor sample.

For example, and without being limiting, the electronic nose may comprise a group of sensors configured to provide scent intensity indications (e.g., according to measured magnitudes and/or measured extinguish rate), or pleasantness indication (e.g., as described in US Patent Publication No. 2012/0143804), such that the electronic signature data may be used to determine one or more olfactive descriptors e.g., using pattern recognition, and/or neural networks, and/or similarity tests.

The term "olfactive perception" refers to the "Naming" of the whole impression from a specific odorant sample obtained from the biologic nose (e.g., panelist), and which is used to provide the whole impression of a certain scent. In other words, in case of measuring an olfactive index i.e., more than two descriptors and their values, the system may suggest several olfactive perception options for referencing the sample.

For example, and without being limiting, an olfactive index defining intensity score is 3, sweetness medium, powdery is high, may refer to "Musk" or "Talcum" notes used mainly in baby products, perfumes, fabric softeners and alike. Another non-limiting example, an olfactive index defining intensity extremely high, animalic high, repulsive high may refers to "OUD" notes mainly used in fine fragrances in the United Arab Emirates and the middle east markets).

Wherein the olfactive perception is presented as a value, the value is composed of: (a) numbers; (b) letters; and any combination thereof.

The term "final score" refers to "final grade" of the measured sample. This grade is an objective grade, yet meaningful to professionals or non professionals like consumers. In order to set the final score, each olfactive descriptor gets its importunacy level (i.e., weight) in the calculation of the final grade. The final score (FS) may be determined in different ways, including but not limited to, by using one or more of the following: (i) each olfactive descriptor ($D_i$) has its predefined importance (weight, $W_i$) in the final score based on final application (k) e.g., $$FS^{(k)} = \sum_{i=1}^{N} W_i \cdot D_i$$

where N is the number of olfactive descriptors and i, k, N≥1 are positive integers, such that different scores may be determined for the same sample based on the weights determined for use; (ii) using a kind of "Crowdsourcing" algorithm for integrating the human scoring and impotency of each olfactive descriptor, (iii) the user may build the formulation for the final score according to her needs or preferences. The final score of a scent can assist for example for setting a discrimination method for efficacy test of a home ambiance product, anti scent filter, or for setting a "test kit" for scent perception which may assist, as "first aid measurement" and simple non invasive home test in disease identifications (for example—in disease "A" the intensity sensitivity of a tested person and the olfactive families would have the same importunacy (e.g., weights) in final score, while for disease "B" they would have different importunacy or the final score would have a third descriptor in the equation).

The term "sampling module" refers hereinafter to any module able to transfer and/or to produce a gaseous state sample from a sources or an odorant material and transfer it to the analyzing module.

The term "analyzing module" refers hereinafter to a device intended to measure olfactive descriptors using one or more panelists and/or an electronic signature generated by an electronic nose unit.

The term "electronic nose" refers to a device intended to detect volatile components. For example, and without being limited, the electronic nose may comprise one or more of the following: electric nose sensors; electronic tongue sensors; bioelectronic noses, temperature sensors, humidity sensors, viscosity meters, chromatographic apparatus, mass spectrometers, Infra-Red sensors, FID detectors, PID detectors, chemiresistors, semiconductors; Thin-film metal oxides (MOX); Thick film MOX; conducting polymers (CP); Quartz Microbalance, supramolecular materials; quarts crystal gas sensors, biologic sensor; quantum vibrations sensors; Surface Acoustic Wave sensors, Optical Fiber Sensors, olfactory receptors; trigeminal inspired sensors; sensors inspired by the olfactory system or any other system of a living creature, functional inorganic materials composites, Nano wires, Nanomaterials. The electronic signature may thus be a set (or an ordered sequence) of measurement values obtained from the various sensor of the electronic nose in response to the odorant sample under predefined conditions (e.g., temperature, humidity, pressure, of, or at the surrounding vicinity, of the sensors).

An arrangement/matrix of sensors used in the electronic nose unit to generate a signature may comprise one or more of the above sensors or any combination thereof. These sensor types have different sensitivity, selectivity, robustness and service life characteristics. Furthermore, the analyzing module can operate in different conditions like different temperatures, humidity, flow rate of the samples, size and volume of the samples etc. The choice and combination of conditions and/or technologies depends primarily on the descriptors to be measured. The sensor arrangement may contain different sensors based on their sensitivity so that the system may be adapted to react to a vast scale of descriptors and volatile components in different concentration.

The term "carrier gas" refers hereinafter to a gas or mixture of gases, such as air, helium and nitrogen, etc. that can carry volatile molecules of a sample.

The term "gas phase" relates mainly to liquids evaporating into a gas but may also refers in some embodiment to any material or a mixture of materials in their gas state either in natural condition, or by any manipulation transformed into a "gas".

The term "treating cell" refers hereinafter to a closed chamber utilized to treat an odorant material and prepare therefrom at least one sample for analysis. The sample may consist of one molecule or a mixture of different molecules, may be homogenous or heterogeneous. The treating cell may treat the mixture of the molecule as a whole, or treat each molecule in different stage by different treatments according to the needs.

The term "scent" refers hereinafter to any volatile material, or mixture of materials perceived by an organism, mainly by humans, but can refer also to any other leaving creature, perceived by the Olfactory cells, trigeminal cells, taste sense, VNO organ (Vomeronasal Organ) and/or other, as scented or not, pleasant or unpleasant, activating the sense of smell and/or any other behavioral activity or predefined information coming out from the volatile material. "Scent" may refer to an odor, odorant material, smell, fragrance, aroma, the medium or "source". In case of a "source" this may refer to an object; a living creature, including microorganisms; a plant or any of its parts; an environment; and any combination thereof.

The term "sniffer" refers to any object unit or tool enabling a scent to be perceived by a panelist nose including but not limited to smelling strips, scent absorbing materials including but not limited to papers and cotton, cones, fork like tubes, masks, or any other object, units, or tools enabling the a scent to be perceived by the biologic nose/panelist.

The term "panelist" refers to any organism, leaving creature including but not limited to humans, dogs, cats etc.

The term "specific situation" refers herein to different information, verbal or visual, about the surrounding like for example and without being limited, a presence of illegal substance, a danger, illness, a picture, image, brand image, a decision making like confirming a QC of a product, verbal information and suchlike.

The sample provided to the electric nose and to the biologic nose/panelists for analysis may be obtained from odorant material which is naturally in a gaseous state (e.g., H2S or a mixture of a factory emission which is already in its gas state). In the following non-limiting examples perception of human subjects (panelists) is used to obtain olfactive descriptors, however, in possible embodiments any other perception of living organism may be used. For example, the scent descriptors may be replaced by measurements of brain activity, sexual activity, behavioral activity etc, which may be also used for a human subject (i.e., instead of asking the human panelist intensity of a scent brain activity measured responsive to the specific odor may be used).

The sampling stage may comprise conversion of a liquid (or solid, or semi-solid, soft solid, suspension, emulsion or gas) sample into a gas phase, optionally and in some embodiments preferably without application of any external field (e.g., heating), but rather by increasing flow rate, surface area etc., enabling substantially fast evaporation, e.g., by stirring and/or streaming the liquid sample in a manner increasing surface area exposed for vaporization.

When a certain equilibrium state is obtained, the gas sample proceeds for the testing stage: the gas sample is divided into two or more spatially separated flows, one is directed to the electronic analysing/sensing unit (e.g., electronic nose device and/or arrangement of sensors capable of measuring different chemical and/or physical properties of the samples odorant), and the other is directed towards a panelist (e.g., free space in the vicinity of the panelist, or by using one or more sniffers). The sensing unit generates a respective odorant signature (electronic pattern) and the signature data is received at a computer device, and the panelist provides the values for the predetermined number of descriptors which are input into the computer device, which are used to create a corresponding record for the database. In some embodiments, the sample may be further treated to conduct several manipulations on sample like for example and without being limiting absorb/add humidity, electrically charge etc the sample.

The gas sample may be provided to the panelist in various ways, such as, but not limited to, free space environment (or cotton like medium or smelling blotter), tephlon flexible tube with two teeth fork like split which would enter into the panelist's nose, a cone or another shape that enable the panelist to sense the same vapors, as the electronic nose detects.

The signature generated for each tested odorant may combine measurement data acquired from a plurality of sensor units operable to measure different properties of the sampled odorant, such as, but not limited to, chemical properties (e.g., atom/molecular elements comprised in the sample), physical properties (e.g., thermal, electrical, optical).

The descriptors data may comprise ratings of various olfactive indices obtained from human subjects exposed to samples of odorant materials such as scent intense, scent pleasantness, scent diffusion rate, emotional association, cognitive perception, behavioural activity like wakefulness and suchlike. Whenever more than one olfactive descriptor is obtained from the panelist(s), then at least one olfactive index and/or and final score are determined based on the olfactive descriptors. The olfactive descriptors and/or the at least one olfactive index and/or final score may be determined using machine learning and human panel/crowd sourcing. For example, and without being limiting, the final score may be determined by at least one of the following schemes: (i) each olfactive descriptor has its predefined importance (weight) in the final score based on the final application; (ii) using a type of "Crowdsourcing" algorithm e.g., integrating the human scoring and importance of each olfactive descriptor obtained over a data network (e.g., Internet); and (iii) using user defined formulation for the final score according to user's needs or preferences.

The database created by the data obtained from the panellists/professionals and the electronic nose unit may then be updated by users. The computer creating/updating the database may be configured as an expert system capable of self-learning and thus updating the selected model for scent measurements (olfactive descriptors, olfactive index, olfactive perception/naming and final score).

The database may be used for identifying/classifying an unknown sample. To this end, the odor (e.g., gas-phase) sample is supplied to the electronic nose unit which generates a signature, and the computer compares the generated signature to a plurality of recorded pre-analyzed signatures stored in the database, using a fitting approach to identify the best fit between the measured signature and the stored signatures and thus determine similarity of sample to one or more of the recorded samples.

In some applications, the system of the invention for creating a database comprises:

an input unit for feeding an odorant sample;

an electronic sensing unit configured and operable for receiving the sample and generating an electronic signature characterizing the received sample;

a sample guiding unit for receiving the odorant sample and guiding a first portion of the sample into the electronic sampling unit and guiding a second portion of the sample towards an outlet, thereby enabling one or more users and/or panelists to be exposed to said sample emerging from the outlet;

a control unit comprising a first data input for receiving data indicative of an electronic signature generated by the electronic sensing unit and a second data input for receiving data from the one or more users/panelists indicative of a plurality of predetermined descriptors characterizing the sample to which the user is exposed, thereby enabling creation of a data record including first and second characterizing data corresponding to the same sample.

The input unit of the system may comprise a sampling unit for receiving an odorant sample in its initial liquid, solid, semi solid, emulsion, suspension or aerosol phase and transforming it into a gas phase sample to be fed to the sample guiding unit.

The sensing system may comprise: an analysis unit connectable to a sensing unit and being in data communication with a storage device where the database is maintained (e.g., via a network), the analysis unit being operable to receive the signature data from the sensing unit and access the database to analyze the stored data records associated with one or more of the recorded pre-analyzed signatures and identify the signature having a certain level of similarity to the signature received from the sensing unit, and generate data indicative of the corresponding odorant material, thereby enabling to associate a sample being processed by the sensing unit and the known olfactive descriptors of odorant material.

The control unit may comprise a statistical data processing module configured to process the electrical signature and the olfactive descriptors obtained from the panellists and generate normalized/statistical processing electronic signatures and normalized/statistical processing olfactive descriptors data The control unit may further include an olfactive index module, which in case of more than one olfactive descriptor, is configured to determine at least one olfactive index from the signature, and/or from the olfactive descriptors obtained from the paneliss/s, by presenting the different olfactive descriptors and their values.

The control unit may also comprise an olfactive, perception module configured to determine olfactive perception based on the different descriptors suggested above, and using a the "likelihood" and fitting approach to identify the best fit between the proposed olfactive perception above and the accumulated database by users and crowds sourcing which would enter, as part of the descriptors and sample's information, also naming, usage, markets etc—olfactive perception can be generated The invention, in some of its embodiments, provides for the detection, forecasting and evaluation of objective olfactive perception. More specifically, in some embodiments the invention relates to a system and method for collecting a sample of volatile components and analyzing their perceptive descriptors and olfactive perception based on chemical composition and other properties.

In some embodiments, the system may be associated (e.g. comprises or connected to) with an automatic calibration unit adapted to automatically clean and calibrate the electronic nose unit based on pre-defined references. It is, however, noted that calibration may be dependent on different criteria's, such as but not limited to: sensor's technology, sensor's chemical composition, odorants chemical and/or physical characteristics, sensor's age, number of samples to be measured, etc. Therefore, in some preferred embodiments calibration of the sensors of the electronic nose is not needed.

At least one sampling module may be used to draw at least one sample of volatile components of an odor, homogenous or heterogeneous from a source. At least one treating and conditioning cell may be used to receive at least one sample and prepare it for analysis. At least one split may be used to split the scent flow for analysis by the electronic nose unit and the panelists. Characteristics of sample analysis environment (e.g., sensor chambers and/or panelists' booth) in which the sample is being analyzed, may be adapted to conform to different conditions like surrounding temperature and humidity, giving a finger print to at least one sample. At least one sniffer may be used to send a scent to a panelist.

In some embodiments, the system is implemented without a split e.g., after completing the construction of the scent database and using the database for scent descriptor analysis and/or identification without requiring the inputs of the biologic nose/panelists.

The source of odorant material may be selected from of the following: (a) gas; (2) liquid; (3) solid; (4) semi solid; (5) soft solid; and any combination thereof, homogenous or heterogeneous. Alternatively, the source of odorant material may be selected from of the following: (a) an object; (b) a living creature, including microorganisms; (c) a plant or any of its parts; (d) an environment; (e) breath, and any combination thereof.

In some embodiments, the system comprises a portable sampling apparatus or absorbing medium (e.g., sampling bag such as a TEDLAR bag) adapted to draw at least one sample of volatile components from a source.

A treatment cell may be used to prepare a sample from the odorant material by means of a surface area expansion/ streaming process during which an equilibrium point of odorant concentration is reached inside the treatment cell. When said equilibrium point is reached the sample is streamed from the treatment cell through an output line for analysis by the analysis module at 100% sample concentration. For example, and without being limiting, if the odorant material is in liquid state, the treatment cell may comprise circulation pump and circulation line for circulating the odorant material through the volume of the treatment cell. A concentration sensing unit installed inside the treatment cell may be used to monitor the concentration of the odorant material inside the internal environment of the treatment cell to determine if the desired equilibrium point has been reached. In some embodiments, the concentration sensing unit is adapted to identify concentration changes of odorant material inside the internal environment of the treatment cell, and to determine that equilibrium point has been reached once no further changes are identified.

The treatment cell may be further adapted to dilute the sample streamed therefrom for analysis by mixing the streamed sample with a predetermined amount of diluting gas. For example and without being limiting, in some embodiments the sample streamed through the output line from the treatment cell may comprise a flow rate sensing device adapted to measure the flow rate of the streamed sample. A dilution line connected to the output line may be used to mix the sample streamed through the output line with a stream of diluting gas (e.g., air) streamed into the output line at certain flow rate determined according to the flow rate of the streamed sample, as measured by the flow rate sensing device. In this way, for example, if the flow rate of the diluting gas streamed into the output line equals to the flow rate of the streamed sample as measured by the flow rate sensing device, the sample concentration streamed to the analysis unit will be about 50%. By controllably adjusting the flow rate of the diluting gas the concentration of the odorant sample streamed to the analysis unit may be adjusted to provide any desire concentration level for the analysis.

In some embodiments, the treatment cell comprised at least one of: a heating device; a humidifier; a desiccant; a pressure applying device (e.g., pressure pump); an electrical charge applying device; a sample ionization device; an absorbent cell; a vaporization cell; and/or any combination thereof.

After completing the construction of the scent database the system may be adapted for scent descriptor analysis of an odorant sample introduced to the sample module by comparing the signature generated by the electronic nose to the signatures of or pre-analyzed odorant materials stored in the database by using different technics, including but not limited to: similarity test and/or, pattern recognition techniques, and/or neural networks etc. The system may be further adapted to determine the percentage of the different volatile components in the sampled odorants by, for example and without being limiting, comparing the portions of the signature obtained for an odorant sample indicative of measured magnitudes to the same portions of the signatures of the pre-analyzed odorant materials stored in the database and which passed a relevant statistical test, like for example, and without being limited, the comparison test.

The system is adapted in some embodiments for ranking at least one sample in a different indices' including, but not limited to, hedonic index. By way of a non-limiting example, this hedonic index may be used for choosing relevant fragrances for scent branding for a store wanting it's customers to feel comfortable and relaxed. Another non limiting example may include the customization of a fragrance.

In addition, the system may be adapted to formulate the composition of volatile components in order to create a specific olfactive perception. For example, and without being limited, the system may be adapted to store and maintain one or more samples of the pre-analyzed odorant materials, and by using a suitable manifold for flowing quantities of at least some of the stored samples according to the percentage determined for each of the volatile components to a mixing vessel, to construct a formulated composition according to an electronic signature of a new odorant sample, and/or desired olfactive descriptors and/or olfactive perception properties defined by a user of the system.

In some embodiments the system may be adapted to generate an olfactive perception map presenting (e.g., by 2D or 3D graphs) the perceptive descriptors levels determined by the panelists and/or as determined by forecasting from the electronic signature. The system may be further adapted to different applications. For example without limiting, create a visual display of the olfactive perception e.g., by assigning a specific color to each perceptive descriptor and indicating the determine level of each descriptor by the intensity of the color associated with it. Accordingly, system may further comprise a human machine interface (HMI) for receiving data inputs and instructions from a user and for presenting to the user data on a display device of the HMI.

In some embodiments the olfactive descriptors and/or olfactive index, and/or olfactive perception and/or final score is presented in a way selected from: (a) numerical; (b) graphical; and any combination thereof.

In some embodiments the system further comprises at least one camera adapted to take images of the source of at least one odorant sample. Accordingly, in some possible embodiments one or more of the database records may further comprise one or more images, taken by the camera, and which are associated with the sample source of the odorant material. Alternatively, the system of the invention may be integrated inside a camera, with, or without the database (e.g., the database may be remotely accessed over a computer network such as the Internet).

In some embodiments the system may further comprise at least one sound recording device, adapted to record audio signals of the sample source of the odorant material of at least one sample and record the audio signals in the respective database record. The system may further comprise a transmitter (e.g., using WiFi or Bluetooth) for sending data associated with the odorant sample for recordation in the respective database record, in case said database is hosted on a remote system.

In some embodiments the system may further comprise at least one global positioning system (GPS) adapted to allocate the exact coordinates of the sample source of at least one sample and recording the exact location in the respective database record.

The system may comprise an apparatus for creating mixtures of volatile components to create a specific olfactive perception according to a specific entered olfactive perception, wherein the apparatus stores at least two volatile components.

In some embodiments the system is adapted to alarm on the presence of harmful volatile components (for example and without limiting chlorofluorocarbons and chlorocarbons, benzene and its derivatives, methylene chloride, methylene chloride and other) identified in at least one sample based in their olfactive descriptors and/or olfactive index. The system may be further adapted to alarm on identification of olfactive descriptors reflecting harmful, illegal source or a specific situation.

The system may be adapted for formulating a composition of a personalized scent. Example may include, but not limited to a system which may comprise at least one Human Machinery Interface (HMI) adapted to receive information regarding preferences of olfactive perception, or preferences of olfactive descriptors. It is important to note that in case of only one olfactive descriptor, in some embodiments, possibilities may be too vast without real meaning to the user and the control unit may be adapted to formulate a composition of volatile components to give the desired olfactive perception received via the HMI. For example, the control unit may be configured to extract from the scent database records that have olfactive descriptors and that are associated with the desired olfactive perception(s) and determine a composition of volatile components that can be used to construct the desired olfactive perception(s).

The system may be also used to create an olfactive perception, by obtaining an electronic signature of an odorant material and using (for example, and without being limited, by comparison) the obtained signature to find at least one similar signature of pre-analyzed odorant materials stored in the database, obtaining at least two values of olfactive descriptors (and optionally more) associated with the at least one similar signature (optionally more), formulating at least one olfactive index from at least two values of olfactive descriptor and determining an olfactive perception according to the at least one olfactive index (optionally more than one).

In some embodiments the system may comprise an apparatus for creating smells according to a specific entered olfactive perception. The system may thus be adapted to store at least two volatile components.

The system may be used for changing a specific olfactive perception of a source by using the electronic signature obtained for the source for calculating and formulating an olfactive perception by using a suitable algorithm needed to change the specific olfactive perception to a third new olfactive perception which, for the user, perceptually speaking, is different enough from the original olfactive perception. Accordingly, in some embodiments there is provided a method for neutralizing unpleasant scents.

The system may be used to evaluate an olfactive perception of an object by drawing an odorant source to the sampling module of the system from the object, operating the system to determine an olfactive perception associated with the odorant source according to the electronic signatures measured by the system's analyzing module and/or according to the different descriptors suggested above and using suitable mathematical processing, such as but not limited to the "likelihood" and fitting approach, to identify the best fit between the proposed olfactive perception above and the accumulated database by users and crowds sourcing which would enter, as part of the descriptors and sample's information, to generate the olfactive perception.

The system may be used to crate and/or evaluate an olfactive perception from at least two odorant sources, in some embodiments more by taking at least two samples of the at least two (same) odorant sources by the system, processing electronic signatures of the at least two samples to identify similar signature of pre-analyzed odorant materials in the database, and retrieving the olfactive perception of at least two objects and calculating and formulating the new olfactive perception by mixing in different ratios the two samples. The calculating and formulating processes are based mainly, but not only, on predefined preferences and the olfactive descriptors of each component in the new olfactive perception.

The system may be further adapted to notify about places wherein products having a certain olfactive perception, identified by the system, may be purchased.

In one aspect, there is provided a system for creating a scent database, the system comprising an electronic sensing unit configured and operable for receiving a gas-phase odorant sample and generating an electronic signature characterizing the received sample, a sample guiding unit for guiding first portion of the sample into the electronic sampling unit and guiding a second portion of the gas phase sample towards an outlet, thereby enabling one or more users to be exposed to the gas-phase sample, a control unit comprising a first data input for receiving data indicative of the electronic signature generated by the electronic sensing unit and a second data input for receiving data from the one or more users indicative of a plurality of olfactive descriptors characterizing the sample to which the users are exposed, thereby enabling creation of a data record including first and second characterizing data corresponding to the same sample.

The system may further comprise a sampling unit for producing a gas phase sample in certain concentration from an odorant material.

Optionally, and in some embodiments preferably, the control unit is configured to determine one or more olfactive descriptors from the electronic signature, and, in some embodiments, to add the determined olfactive descriptors to the respective data record.

In some embodiments the control unit comprises at least one of the following:
   an olfactive index module configured to determine at least one olfactive index to be added to the respective data record, the at least one olfactive index being a combination of values of two or more olfactive descriptors in a meaningful manner for a specific product or application associated with the odor sample, and in some embodiments to be added to a data record; and
   an olfactive perception module configured to determine at least one olfactive perception, which may be added to the respective data record, the at least one olfactive perception is determined based on the olfactive descriptors.

The control unit may be configured to determine one or more scores, each being a weighted average of ratings of the olfactive descriptors and being indicative of importance of sampled odorant to a specific application, and to add the determined scores to the respective data record.

Optionally, and in some embodiments preferably, the control unit is configured to include in the data record at least one sensorial indication from the biologic nose arrangement being indicative of cognitive perceptions associated with the sample.

In some embodiments the sampling unit is configured to maximize concentration of odorant vapors in the sample. For example, and without being limiting, concentration may be maximized by reaching an equilibrium state between liquid and the gas phase of the odorant material e.g., the equilibrium point may be achieved by using surface area expansion process applied to the odorant material, and/or by circulating the odorant material inside a closed vessel.

In some embodiments a sample dilution unit is used to controllably mix, automatically or by the operator, the sample by applying physical manipulations like those based on the ventury principal, or dissolving, Chemical manipulations like absorption and controlled release, enabling the dilution of the gas. The diluting gas may be flowed at predetermined flow rate to provide a predetermined sample dilution ration.

In another aspect the invention relates to a method of constructing a scent perception database, comprising selecting an odorant material from a predetermined set of odorant materials, splitting a stream of a gas-phase sample of the selected odorant material to a scent analyzing unit comprising between an electronic sensor arrangement and a biologic sensor arrangement, responsive to the gas-phase split odorant sample, receiving measurement data from sensor elements of the electronic sensor arrangement, and generating an electronic signature data indicative thereof, and at least one olfactive descriptor from the biologic sensor arrangement, generating at least one olfactive index by combining values of two or more olfactive descriptors in a meaningful manner for a specific product or application or action associated with the odorant sample, recording the electronic signature, the at least one olfactive descriptor, and, in case of more than one descriptor, the at least one olfactive index, in a data record of said data base, the database record being associated with the material, and repeating the above steps for other odorant materials in the predetermined set of odorant materials.

The method may further comprising preparing the gas-phase sample by maximizing concentration of vapors of the selected odorant material in the sample e.g., by reaching an equilibrium state between liquid and the gas-phase of the selected odorant material to thereby maximize the concentration of odorant vapors in the sample. Optionally, and in some embodiments preferably, the equilibrium point is achieved inside a closed vessel by at least one of circulating the selected odorant material inside said vessel and applying an area expansion process to the odorant material inside said vessel.

The method may comprise one or more of the following: determining at least one olfactive descriptor from the electronic signature and adding it to the data record; determining at least one olfactive perception based on the olfactive descriptors and add it to the data record; determining at least score being indicative of importance of the sampled odorant to a specific application and optionally adding it to the data record, the at least one score being a weighted average of the olfactive descriptors; and determining at least one sensorial indication from the biologic nose arrangement being indicative of cognitive perceptions associated with the odorant material.

In some embodiments the method comprises using the data base to analyze new odorant materials, and optionally adding a new data record to the data base for any new odorant material analyzed using the database.

In yet another aspect there is provided a system for analyzing a perception of a scent comprising an electronic sensing unit configured and operable to receive a gas-phase sample of the scent, measured and characterizing features of the received sample, and generate an electronic signature indicative thereof, a scent database comprising a plurality of records each being associated with a predetermined odorant material and comprising at least: an electronic signature obtained from a gas-phase sample of said odorant material by said electronic sensing unit, at least one olfactive descriptor generated by a biologic nose responsive to said gas-phase sample, and a control unit having access to said scent database and configured to identify the best fit between the measured signature and the signatures stored in the database and generate at least one olfactive descriptor for said scent based on at least one of the best fit signature and the olfactive descriptors associated with said best fit signatures.

The control unit may comprise an olfactive index module configured to determine at least one olfactive index for the scent, the at least one olfactive index being a combination of two or more olfactive descriptors in a meaningful manner for a specific product or application associated with the scent.

Optionally, and in some embodiments preferably, the control unit comprises at an olfactive perception module configured to determine at least one olfactive perception determined based on the olfactive descriptors; and The control unit may be configured to determine one or more scores, each being a weighted average of ratings of the olfactive descriptors and being indicative of importance of sampled odorant to a specific application.

In some embodiments the control unit is configured to determine at least one sensorial indication from the measured signature being indicative of cognitive perceptions associated with the sample.

BRIEF DESCRIPTION OF THE DRAWINGS

In order to understand the invention and to see how it may be carried out in practice, embodiments will now be described, by way of non-limiting example only, with reference to the accompanying drawings, in which like reference numerals are used to indicate corresponding parts, and in which:

FIGS. 1A and 1B schematically illustrate a system for constructing and using a global database of scents according to some possible embodiments, wherein FIG. 1A is a general block diagram of the system and FIG. 1B shows a possible implementation of the sample module;

DETAILED DESCRIPTION OF EMBODIMENTS

Figure 1A:
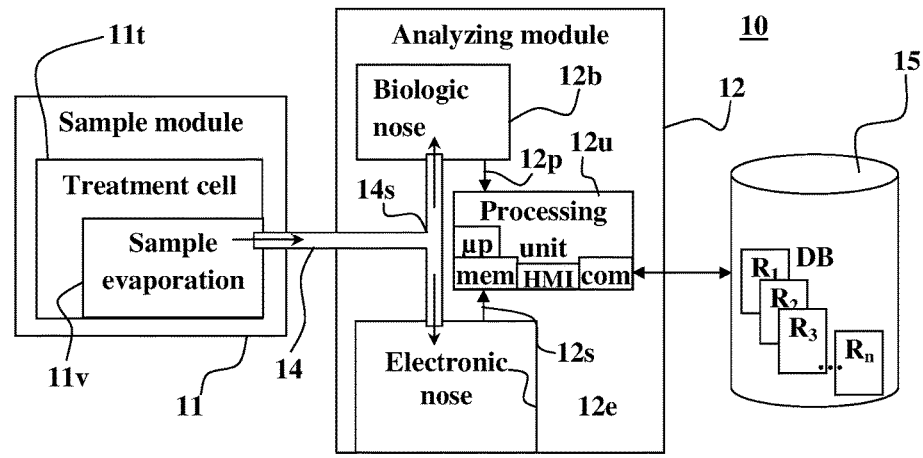

The various embodiments of the present invention are described below with reference to FIGS. 1 through 5 of the drawings, which are to be considered in all aspects as illustrative only and not restrictive in any manner. Elements illustrated in the drawings are not necessarily to scale, emphasis instead being placed upon clearly illustrating the principles of the invention. This invention may be provided in other specific forms and embodiments without departing from the essential characteristics described herein.

In general, the present invention provides a system for the production, detection and evaluation of a scent perception and more particularly the olfactive descriptors of a scent. In possible embodiments the system may comprise at least one sampling module adapted to draw at least one sample of volatile components of an odor, homogenous or heterogeneous, from a source; (b) at least one treating and conditioning cell adapted to receive at least one sample and prepare it for analysis; (c) at least one split adapted to split the scent flow to the next units; (d) at least one analyzing module adapted to generate an electronic signature for at least one sample; (e) at least one sniffer adapted to send a scent to a panelist for evaluation.

The electronic sensor unit comprises a plurality of sensors each adapted to identify presence of a predetermined material or molecule, or group of chemical or physical properties, in a sample introduced thereto, and generating data indicative thereof. The data obtained from the plurality of sensors is used to generate a unique electronic signature associated with the sampled odorant and further processed to compute descriptors (e.g., intensity, pleasantness, and suchlike) associated with the sampled odorant. Statistical analysis techniques may be used to process the computerized descriptors and the descriptors obtained from the biological sensors and generate a set of normalized descriptors to be recorded in the database together with the computerized descriptors and the panelists' descriptors.

The descriptors may be then used to determine a set of indices associated with the sampled odorant. Each olfactive index comprises a combination of two or more of the descriptors from the panelists' descriptors, the computerized descriptors, and/or the normalized descriptors. The descriptors may be also used to determine one or more scores for each odorant sample each being indicative of the importance of the odorant sample to a specific application (e.g., shampoo scent, laundry scent, incense, and suchlike).

The system may used to define odor perception at equilibrium point of odorant concentration and establish a scent perception measure relative to the determined equilibrium point, and/or relative to smaller concentrations of the odorant in the sample obtained relative to said equilibrium point concentration.

With reference to FIG. 1A, in some embodiments odorant materials are sampled and analyzed using a system 10 comprising a sample module 11 operable to receive odorant material and produce an odorant sample therefrom, an analyzing module 12 operable to receive the odorant sample and split it between biological nose 12$b$ and electronic nose 12$e$ modules operable for analyzing the odorant sample and generate data indicative thereof. The biological nose module 12$b$ may be implemented by one or more panelists (e.g., using sniffers) used to provide evaluation of the odorant by one or more olfactive descriptors 12$p$ (e.g., intensity, pleasantness, diffusion, and suchlike). The electronic nose 12$e$ may have unique characteristics enabling the detection of olfactive descriptors. The electronic nose may also be implemented by any suitable commercially available scent detection device, having an automatic calibration and cleaning system to specific predefined references utilizing one or more arrangements of sensors capable of identifying (e.g., based on chemical, physical, and/or electrical properties) presence of one or more odorant materials in the introduced sample, and generate a unique electronic signature 12$s$ indicative thereof.

The analyzing unit 12 further comprises a processing unit 12$u$ configured to receive and process the one or more olfactive descriptors 12$p$ from the biologic nose 12$b$ and the electronic signature 12$s$ from the electronic nose 12$e$, and generate a corresponding data base record $R_i$ comprising said olfactive descriptors 12$p$ and electronic signature 12$s$, and additional data associated with the odorant sample and generated by the processing unit 12$u$. The generated data base record $R_i$ (where $i \geq 1$ is a positive integer) is transferred from the analyzing 12 for storage in a database system 15, which may be located remotely (e.g., remote server accessible via a communication network). Alternatively, in some possible embodiments, the database system 15 may be implemented as a part of the odorant analysis system 10.

The processing unit may be a type of computer (e.g., PC, smart device) comprising a processing utility (µp), one or more memories (mem, e.g., RAM, ROM, EPROM, FLASH), a human machine interface (HMI), and a communication module (com) for communicating data with the database system 15 (e.g., over USB or parallel data communication line, over a computer network, or using wireless communication such as bluetooth, WiFi, ZigBee). The HMI unit may comprise at least one input device (e.g., keyboard, pointing device and suchlike) and at least one output device (e.g., speakers, touch screen, and suchlike).

In some embodiments the sample module 11 may comprise a treatment cell **11*t* operable to receive an odorant material and produce a sample thereof at a certain concentration equilibrium point obtained thereinside, for example, and without being limiting, by applying a sample evaporation process 11*v*. It is important to note that this process of evaporation can be done in one or more vessels operating at the same time or not. The equilibrium point may be achieved by a surface area/stream expansion process during which concentration of the odorant material inside the space of the treatment cell 11*t*** is increased until the desired equilibrium point is reached.

Figure 1B:
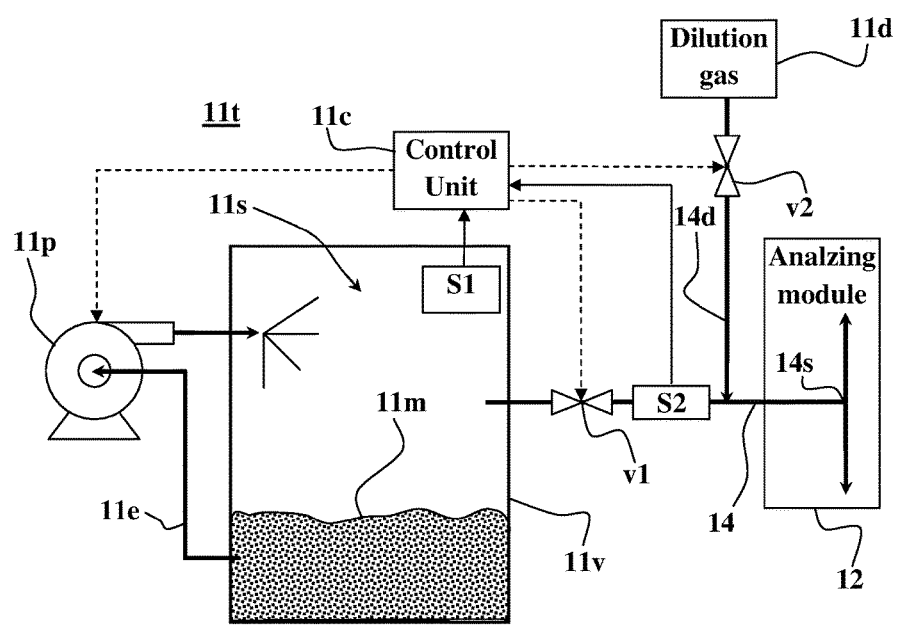

By way of example, and without being limiting FIG. 1B demonstrates a possible embodiment of the treatment cell **11*t*, utilizing a circulation pump 11*p* and a circulation line 11*e* to circulate an odorant material 11*m* provided in liquid state inside an evaporation vessel 11*v* of the treatment cell 11*t*. The circulated odorant material may be sprinkled inside the treatment cell 11*t*, to thereby increase the concentration of the odorant material 11*m* in the internal volume 11*s* of the evaporation vessel 11*v***, until the desired equilibrium point is reached.

For example, and without being limiting, the evaporation vessel **11*v* may comprise a concentration sensor S1 adapted to measure the concentration of the odorant in the volume 11*s* of the evaporation vessel 11*v* and generate measurement data indicative thereof for determining when the desired equilibrium point has been reached. A control unit 11*e* may be used to monitor the measurement data from the concentration sensor S1 and determine when the desired equilibrium point been reached once it is determined by the control unit 11*e* that the concentration of the odorant in the volume 11*s* inside the evaporation vessel 11*v* is not increasing for some predetermined duration of time. When determining that the equilibrium point been reached (i.e., 100% odorant concentration in the sample), the control unit 11*e* may stop the operation of the circulation pump 11*p*, and open a control valve V1 provided in an output line 14 used for discharging the sample from the treatment cell 11*t* and deliver it to the analyzing module 12**.

As seen in FIGS. 1A and 1B, in a way of example and without being limiting, the output line 14 may includes a split ("T" junction) **14*s* wherein the sample streamed from the treatment cell 11*t* is split between biologic nose 12*b* and the electronic nose 12*e*. the split 14*s* may be designed to flow a certain portion of the streamed sample to electronic nose 12*e*, which may require relatively small amounts of the sample to generate the electronic signature, and a more significant portion of the sample to the biologic nose 12*b*** to be analyzed by a number of panelists, as may be needed.

The concentration of the odorant in the sample may be controllably changed by mixing it with a diluting gas (e.g., air, shampoo vapors, solvent etc) **11*d*. For example, and without being limiting, the output line 14 may comprise a flow meter S2 for measuring the flow rate of the sample through the output line 14 and generating data indicative thereof, and the control unit 11*e* may be configured to monitor the flow rate through output line 14 and controllably open valve v2 operable to regulate flow of dilution gas 11*d* through dilution line 14*d* into the output line 14. In this way, based on the data from the flow meter S2 the control unit may regulate the flow rate of the dilution gas and thereby reduce the concentration of the odorant in the sample to a predefined percentage needed for the analysis by the analyzing module 12. In this way the system 10** may be utilized to analyze odorant materials at various different concentration levels, and thereby create a standard for scent perception and odor families similar to the Dravnieks atlas and Jaubert et al experiment. The dilution from the equilibrium condition would in some cases, results in different odor family and different olfactive perception than in the equilibrium state of the same odorant. In other words by similar experiment like Andrew Dravnieks and Jaubert et al did and by setting an equilibrium of different odor materials we can set new method for measuring scent.

Figure 2:
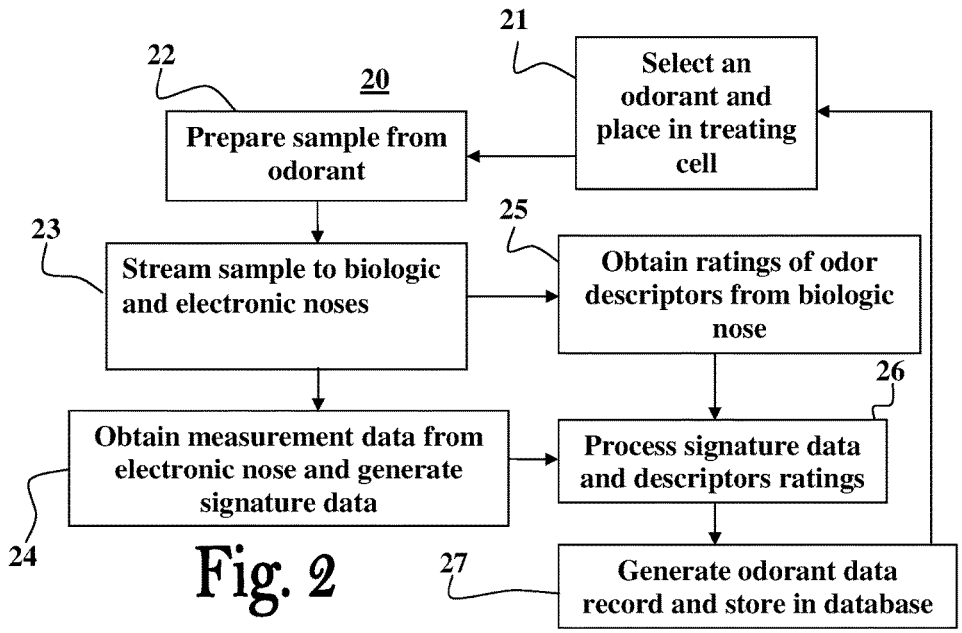
FIG. 2 is a flowchart illustrating a process for construction of a global scents database according to some possible embodiment.

FIG. 2 is a flowchart illustrating a process 20 for construction of a scents database using the system 10, according to some possible embodiment. The process begins in step 21 in which an odorant is selected from a representative group of odorants, like, as a non limiting example—the Jaubert et al references, or from "odor space" and place in the treating cell (**11*t*). Next, in step 22 the odorant sample is prepared from the odorant material and streamed from the treatment cell (11*t*) to the electronic nose (12*e*) and the biologic nose (12*b*) for analysis. In steps 24 a portion of the sample received by the electronic nose (12*e*) is analyzed, and a corresponding unique electronic signature is generated therefrom. In step 25 a portion of the sample received by the biologic nose (12*b*) is analyzed by the panelists, which then provide olfactive descriptors associated with the analyzed sample, and rating (e.g., on a scale from 1 to 10 or −15 to +15 or "no smell" to "extremely strong") for each descriptor. In step 26 the signature data from the electronic nose (12*e*), and the olfactive descriptors rating data from the panelists, are processed by the processing unit (12*u*), and in step 27 the processing unit (12*u*) generates a respective odorant data record ($R_i$) from the processed data and store it in the database (15**).

In some possible embodiments, and without being limiting the processing unit (**12*u*) is configured to generate various additional olfactive data in the processing stage. For example, and without being limiting, the processing unit (12*u***) may be configured to process the electronic signature (e.g., using pattern recognition techniques) and generate a set of machine olfactive descriptors therefrom. For instance, the processing unit may be configured to use additional data from the electronic nose, such as, but not limited to, magnitudes of sensors indications obtained in response to the sample, response time of each sensor, and extinction time of the indications obtained from the sensors. These additional data may be processed by the processing unit and used to generate the machine olfactive descriptors and forecasting.

The processing unit may thus comprise a statistical data processing module (not shown) configured to process the olfactive descriptors obtained from the panellists, the electrical signature and any additional data obtained from the electronic nose, and generate normalized electronic signatures and normalized olfactive descriptors data. The processing unit may further comprise an olfactive descriptor module (not shown) configured to determine at least one olfactive descriptor from the signature and/or in case of more than one signature, from more than one group of sensors, or in more than one sensor's conditions, an olfactive index. The system may further comprise an olfactive perception module (not shown) configured to determine olfactive perception of the analyzed sample based on the different descriptors suggested above and using a suitable mathematical/statistical test like the "likelihood" and fitting approach to identify the best fit between the proposed olfactive perception above and the accumulated database by users and crowds sourcing which would enter, as part of the descriptors and sample's information, also naming, usage, markets etc. The olfactive perception module may be used to generate a desired olfactive perception.

The process in FIG. 2 may be used to improve performance of the analyzing module by identifying descriptors for which there is substantial variance between the computerized descriptors and the panelists' descriptors.

Figure 3:
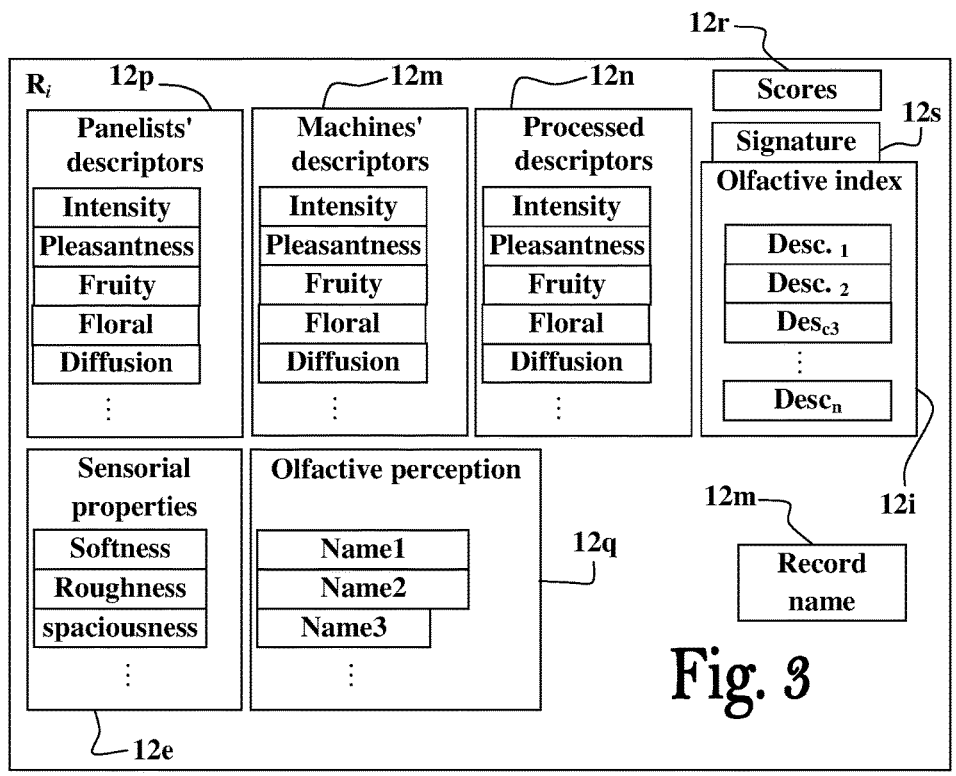
FIG. 3 schematically illustrates a database record according to some possible embodiments.

FIG. 3 demonstrates a possible data record $R_i$ according to some possible. The data record $R_i$ in this non limiting example comprises the record name 12m (e.g., name of the odorant material), the sample electronic signature (and/or normalized signature) 12s, the panelists' olfactive descriptors ratings 12p, the machine's olfactive descriptors ratings 12m generated from the electronic signature and/or the data form the electronic nose, normalized/processed (Macaw descriptors 12n computed by the processing unit (e.g., using statistical data processing) from the descriptors ratings 12p and/or the machine's olfactive descriptors ratings 12m, or a combination thereof. The data record $R_i$ may further comprise one or more olfactive indexes provided by the panelists to characterise the respective sample, where each olfactive index is a combination of two or more of the olfactive descriptors ratings (e.g., intensity 7 and fruity 9).

The data record $R_i$ may further comprise one or more score indications 12r computed by the processing unit to indicate importance of the odor sample to a specific product (e.g., hair conditioner, incense). The score indications may be computed as a weighted average of two or more of the olfactive descriptors ratings, as obtained from different instructions, optionally and in some embodiments preferably, from: the panelists, and/or as determined from the signature data, and/or as normalized by the processing unit.

The weights for each specific product/application/used may be determined by different factors which may include technical and non technical factors. For example, and without being limiting, a candle scent should be diffusive and intense. For some brands and/or users the intensity is the most important while for other the diffusiveness is more important, and the weights are set accordingly. As another non limiting example, predefined weighing formulation can be entered based on a market research or a survey.

The data record $R_i$ may further comprise olfactive perception data 12q obtained from the panellists.

The data record $R_i$ may further comprise sensorial properties 12e obtained from the panelists, or from users concerning the sensorial (e.g., softness, space perception, and suchlike) properties related to the odor sample. An exemplary process for construction of the sensorial properties 12s is explained below with reference to FIG. 5.

Figure 4:
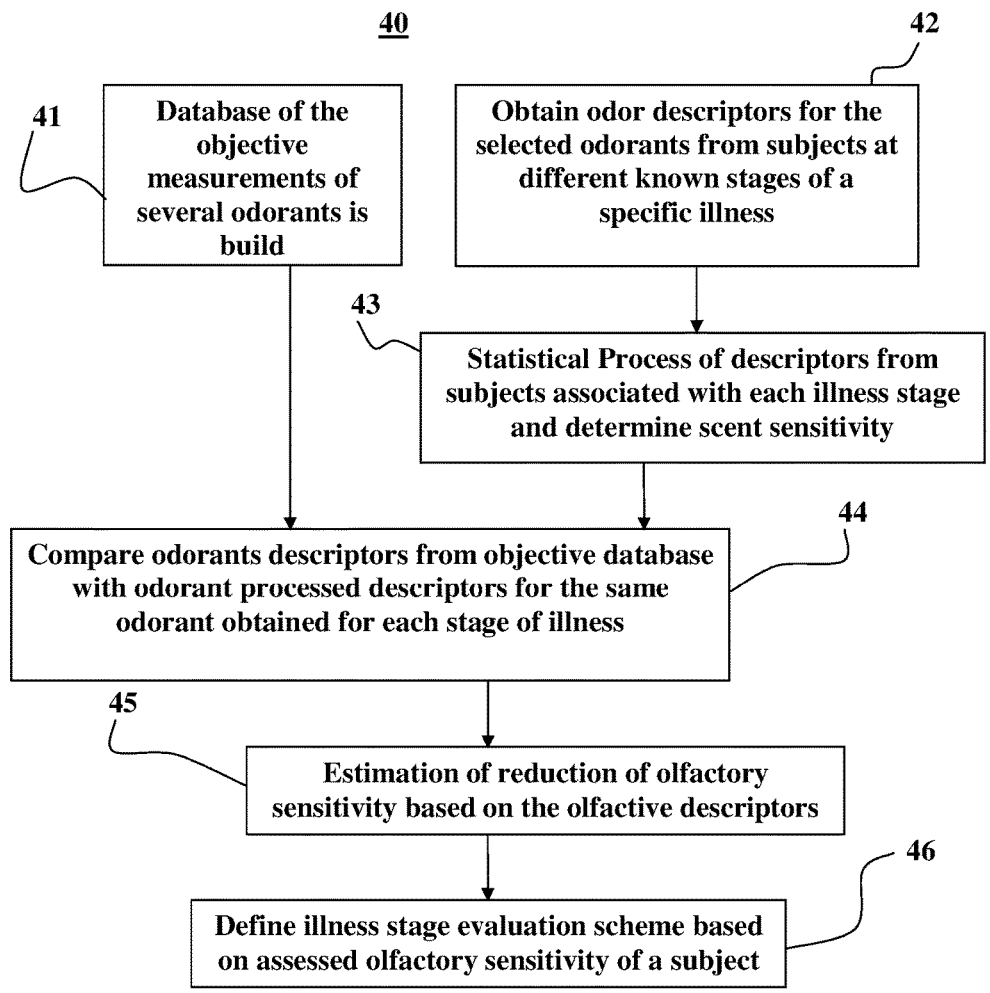
FIG. 4 is a flowchart illustrating use of the system for diagnosis of an illness and possibly an illness stage according to some possible embodiments.

FIG. 4 is a flowchart 40 illustrating use of the system for diagnosis of an illness, and possibly an illness stage according to some possible embodiments. The process begins in step 41 wherein a database (e.g., 15 in FIG. 1) of the objective measurements of several odorants is build. In step 42 olfactive descriptors are obtained for the same odorants of the built database, from subjects at different stages of a specific illness (e.g., Parkinson), and in step 43 the olfactive descriptors obtained from the subjects are processed and associated with each illness stage and a determined scent sensitivity. It is known in the art that different diseases like Alzheimer's and in Parkinson's diseases affect the olfactory sensitivity of a subject. It is generally known that some diseases can be identified by distinct odors, such diabetic, halitosis, cancer, etc. In step 44 the odorant descriptors from the database of the system are compared to the odorant descriptors for the same odorant obtained for each stage of illness, and in step 45 estimation of reduction of olfactory sensitivity is determined for each illness stage based on the comparison results obtained from step 44. In step 46 illness stage evaluation scheme is defined based on assessed olfactory sensitivity of a subject using the estimated reduction of olfactory sensitivity. This enables the construction of a database for disease diagnosis based scent perception and on olfactory sensitivity and the forecasting of an illness and illness stage by simple non invasive device.

The system described herein may similarly used to diagnose illness of a subject according to body odors thereof (e.g., scents sampled form the mouth, body tissues, urine, skin, fecal). More particularly, the construction of the database 15 may comprise analysis of odors of subjects suffering from various types of illnesses, to thereby allow the system to diagnose illness of a subject according to body odors.

Figure 5:
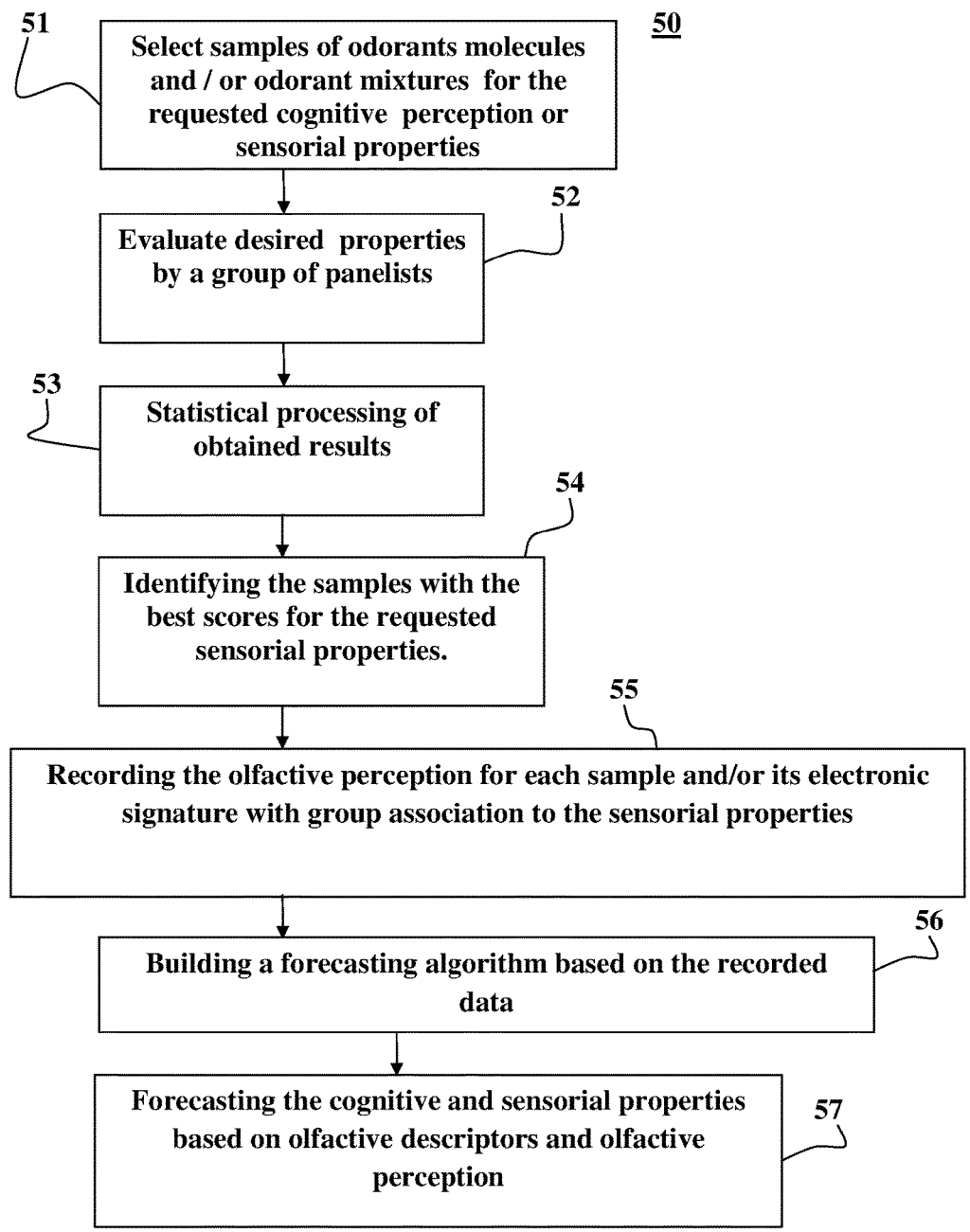
FIG. 5 is a flowchart illustrating use of the system to define cognitive perception and sensorial perceptions associated with odorants.

FIG. 5 is a flowchart 50 illustrating use of the system 10 to forecast and define cognitive or sensorial perceptions associated with odorant materials. The process begins in step 51 wherein odorant samples, pure molecule or mixtures, are selected for evaluation of their sensorial properties. In step 52 sensorial or cognitive properties of the selected sample are evaluated by a group of panelists, and in step 53 statistical processing of obtained results is performed. Next is step 54 the samples having the best scores for the requested sensorial properties are identified, and in step 55 the olfactive perception for each sample and/or its signature is recorded with group association to the sensorial properties. In step 56 a forecasting algorithm is built based on the recorded data which enables expansion of the database to further allow association of odorant samples with sensorial and/or cognitive and/or Hedonic properties. In step 57 cognitive and/or sensorial properties of odorant materials are forecasted by the system based on, olfactive perception and/or olfactive descriptors.

Once the scent database 15 is constructed the scent evaluation system 10 may be implemented without the biologic nose 12b and without the split 14s. Accordingly, the system 10 can be then used to evaluate new scents and products with completely new composition which were not yet introduced to the system and database. This can be done based on the olfactory perception data accumulated in the database. For example, and without being limited, whenever a new odorant is tested a sample of the odorant is produced and streamed to the electronic nose 12e for analysis. The electronic nose generates a respective electronic signature which may be then compared to the signatures stored in the database 15. This comparison may be based on different methods, for example and without being limited, based on pattern recognition or similarity test e.g., Based on similarity test and predefined system condition of operation (sensor's temperature, humidity, flow rate of the sample and suchlike), for example and without being limited, the new sample's records are compared with database records to identify database records which electronic signatures are similar to the electronic signature of the new scent. The different records (like olfactive descriptors and/or olfactive index and/or olfactive perception and/or final score, and/or specific situation) of the database records which electronic signatures were found to be similar to the electronic signature of the evaluated new scent may be then processed (e.g., statistically) to determine one or more olfactive descriptors, and/or olfactive indexes, and/or olfactive perception, and/or score, and/or specific situation characterizing the new evaluated scent.

Figure 6:
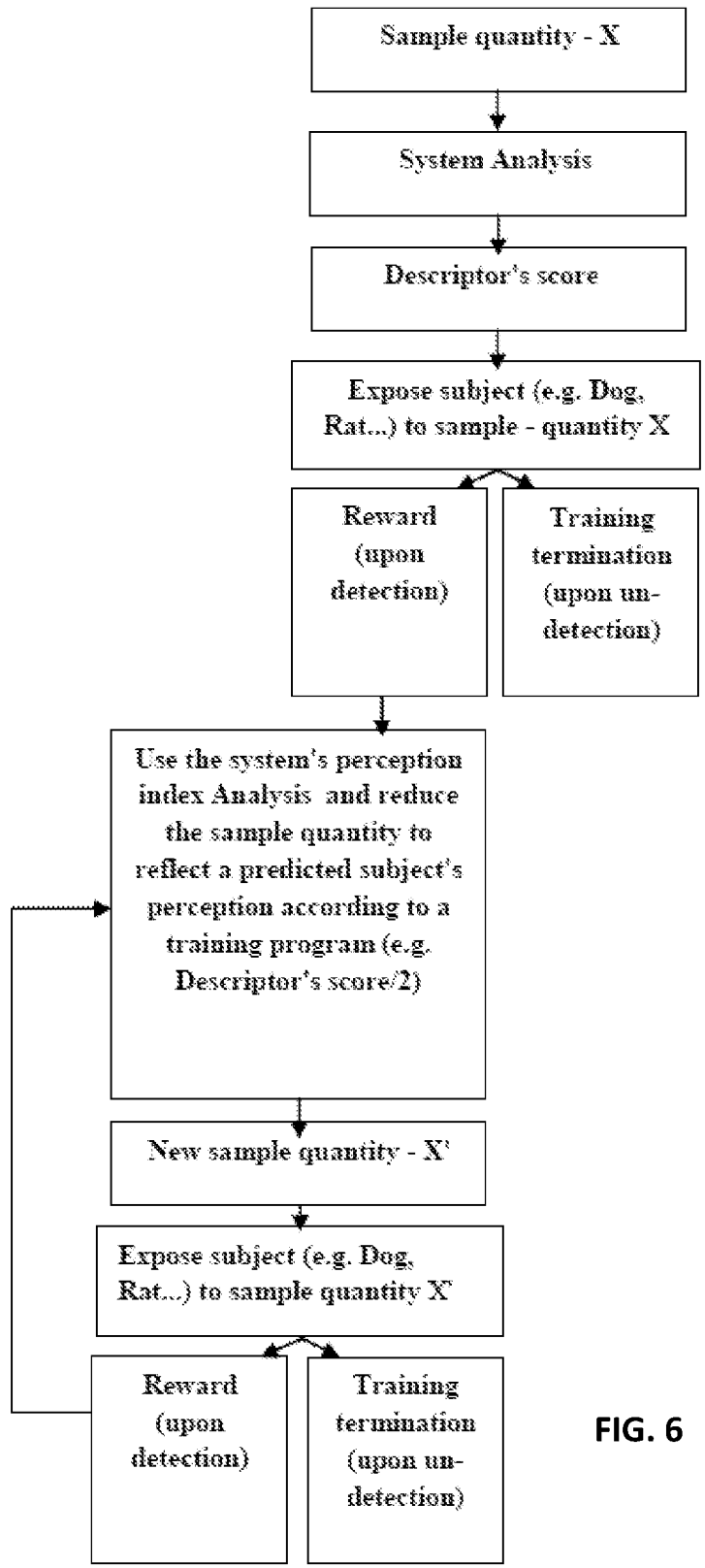
FIG. 6 exemplifies a flow diagram of a process for training an animal (typically a dog) for odor identification.

FIG. 6 illustrates in a self-explanatory manner an example of a training procedure for training a dog or any other animal to be able to identify different odors. This process can be used to determine the minimal sample quantity that can be identified/detected.

Accordingly, the global scent database 15 may be used to determine an olfactive perception of a scent by disintegrating it to olfactive indexes which can be further dissected from olfactive descriptors. This opens a wide range for opportunities, for example, it enables to formulate a scent with different volatile components that will have the substantially similar olfactive perception as of a newly evaluated scent. It is important to note that the new scent formulated based on the database records which signatures comply with a similarity criteria does not need to have the exactly same olfactive perception, chemical compositions, and olfactive descriptors, but all in all will give the similar perception.

The value of an olfactive perception achieved by gathering the values of all the olfactive descriptors of the different components of the new requested olfactive perception, may have identical percentage in the final formulation of the new requested olfactive perception, or different percentage. The decision whether its identical or not is depended on the final requested olfactive perception and the different olfactive descriptors which are being presented in the final formula. The different olfactive descriptors and olfactive indexes and olfactive perception can be composed of letters or numbers or both. The important thing is that the value of a very specific olfactive perception is unique. For example, a lemon cheesecake has a unique value describing its olfactive perception. However, this olfactive perception can be reached, in sufficiently extent, through different combinations of volatile components like is done in some cases of copying an expensive fragrance.

In some embodiments, the purpose of determining an olfactive perception may be for analysis, for creating the perception with different volatile components, and/or for neutralizing an olfactive perception, and suchlike. For example, and without being limiting, the determined olfactive perception may be used for Q.C and/or Q.A, for evaluation of a scent performance and/or the efficiency of a product like scent filters, anti oxidant and suchlike.

In possible embodiments, the system does not include the treating cell. It might be possible that the sample will need no treatment before being analyzed. It is possible that the system/sample module (11) will not include the treating cell but only the sample evaporation unit (11v), or that it may even be implemented without it. This is dependent on many criteria such as, but not limited to, the nature of the sample, the descriptors to be analyzed and forecasted, and the analyzing module and its requirements regarding preparing at least one sample for analysis. At least one sample can be also taken from a source away from the system using a portable sampling apparatus that can take at least one sample of the volatile components of the source. For example, the portable sampling apparatus may comprise the treating cell, but it is not necessarily required. If it does not include a treating cell the sample may be transferred directly to the analyzing module.

According to the olfactive descriptors obtained based on, for example and without being limiting, mathematical test like the similarity test, by using some of the database records a certain picture can be made in association with a newly evaluated scent. For example, and without being limited, an olfactive perception of a cheese cake can give a picture or an image of a bakery or a home kitchen. The decision between the bakery and the home kitchen can be according to additional scents hidden in the main scent of the cheese cake. For example, specific additive usually added only in bakeries or specific smell of a home—without those additive olfactive descriptors. For example, and without being limiting, it might be the best complement for a bakery that the olfactive perception of its cheese cake gives a picture of a home kitchen, as it might imply that they don't use any additives.

The olfactive perception can be described for the user either numerically, alphabetically or graphically or by a combination thereof. In any case, it will present the values or scale of the specific descriptors and in case of more than one descriptor the olfactive index and olfactive perception possibilities or naming and/or final score and specific situation.

In some embodiments the type of treatment that the sample has to go through before entering the analyzing module depends on the sample, the olfactive descriptors to be analyzed and on the type of analyzing module being used etc. It is however possible that no treatment is needed to produce the sample (e.g., in some embodiments in which the sample is provide a gas state).

In possible embodiments the sampling module may utilize a carrier gas. The carrier gas may be used in gas chromatography or in any other suitable way.

The scent evaluation method described herein enables to sharpen the determinants of a certain olfactive perception. For example, if trying to set the olfactive perception of the aroma of a coffee or a wine, one can get sample of at least two wines and find the descriptors in common to both. It is clear that other descriptors may be present in each cheesecake affected by the environment they are in. The more sources obtained the more accurate the perception will be.

As explained hereinabove, in some embodiments the scent analysis method and system described herein is based on measuring the perception of an odor in its equilibrium state between the liquid and the gas/vapor phase (also referred to herein as 100% odor) in predefine conditions like pressure, temperature and humidity. This equilibrium state odor analysis, together with chemical and statistical analysis (e.g., PDA, factor analysis, PCA) enable us setting a group of properties (physical, chemical . . . ) of the molecules with a set a specific olfactive descriptors, like intensity (as in Dravniks and Jaubert et al) which in the future enable to develop a targeted sensing device and which can make the system described above and below even more accurate.

While the system 10 is not suitable to determine "RGB" of scents, it may assist in easy description of scent perception, and may also help in better understanding how our sense of smell works, and in determining how different scent descriptors influence our behavior, psychological condition, preferences, spatial perception (e.g., the size of a room), sensorial evaluation (e.g., descriptors which may help in perceiving a fabric as a softer than other), descriptors describing the smell of a danger or a disease and suchlike.

The present invention may be used for training and evaluation of the sensitivity of one or more panelist, mainly but not limited to human subjects, for human resources decision making for a specific job requires certain sensitivity to scent, like for example training and evaluation system for young perfumers or panelists.

Another not limiting usage of the invention may also be for R&D, Q.A, and/or Q.C, like shelf life testing of a scented product, for batch to batch consistency, for quality control of income raw materials as well as finished products, for scent diffusion, for scent diffusion visualization, for trends analysis, for efficiency tests of different raw materials and/or finished products (like anti oxidation, scent filters pollutant emissions, mouthwash, antiperspirant, etc.), for stability tests in terms of scent, scent tenacity in a medium (for non limiting example synthetic skin), for comparison between suppliers of same material in terms of odor, for detection of Halitosis (Bad mouth breath), and other disease related to mouth breath and scent and/or sensitivity to the sense of smell, and for measuring scent emission from factories.

More particularly, and without being limited, the invention may be used to evaluate scents emission from garbage sites, poultry, meat treatments sites, and suchlike, and for optimization of the localization for scent diffusers and "thermostat" for olfactive descriptors like intensity (instead of timing of on/off each few minutes for the diffusion of scent). The invention may be also used to measure aromas (taste derived from smell), as well for wines, coffee etc.

The sample being tested may also be a filtered sample or air pollution for example in case of efficacy test of scent filters for the industry, the sample may be pure or on a substrate medium like artificial skin, candle, cosmetic product or any other medium supporting the fragrance.

Optionally, and in some embodiments preferably, the scent evaluation system of the invention is implemented as a portable user device, in order to allow users (e.g., aged people or a doctor) to conduct in house tests. The invention may also be used as an in-house research device, for R&D, for building the database 15.

The treatment cell may be configured in some embodiments for diffusion of odorant material in the sample production process. Diffusion may be carried out by any suitable known method and/or technology for scent diffusion that converts liquid, suspension, emulsion or semi liquid into vapors or fine mist or gas like and permits fast evaporation.

This can be done by different ways for example, and without being limited by Micro-Diffusing, micro-mist diffusion systems, Micro Nebulizer technology, dry droplets systems, Fog machine microjetting technology, vibrational systems, and techniques for accelerating evaporation like, for a non limiting example any method for increasing the sample's surface area e.g., stirring, changing the pressure, temperature, by a gas that blows above or inside the liquid phase to speed liquid evaporation or by any other method, physical manipulation, or any other way known in the art to diffuse the sample.

In case of non liquid smell, like for example, a solid or semi solid odorant, the treatment cell may be configured to create scented vapors from the solid or semi-solid sample until reaching an equilibrium between the liquids that evaporates from the solid or semisolid sample and the vapors, and/or until reaching a certain concentration (after dilution by adding a gas and/or any other diluent like the sample's support, air, DPG, Acetone, Ethyl Alcohol, water vapors etc) or another pre-defined physical condition. The diffusion may be done by any known method and/or technology for scent diffusion that can converts the liquid inside the solid or semi-solid sample into vapors.

In case of a gas samples, no evaporation, and there is no need to establish equilibrium point of sample.

The following non limiting Examples relates to possible uses and implementations of the invention.

EXAMPLE 1

The system can be used as a laboratory device to evaluate olfactive descriptors and/or olfactive index, and/or olfactive perception, and/or a score of a perceived odor in a concentrated fragrance oil, cosmetic product, ambient fragrance, toiletries, ambient air etc. Without being limited, the system may also be capable, in some cases, to present graphic and/or numeric values of the scent in means of perception.

Those values and/or graphic descriptions presenting the perception enabling IP protection for the product based on perception (for example, a perfume) or may also be used for quality control (like batch to batch consistency of raw material or finished products), efficiency tests (like of anti oxidant raw material, antiperspirants, scent filters, mouth wash etc), shelf life, fragrance sustainability on the skin, off odor issue in a raw material (which raw material is less odorant), stability test of odors.

EXAMPLE 2

The system enables digital transmittance of olfactive descriptors and/or olfactive perception. For example, and without being limiting, at location A, an olfactive perception of a rare flower, is received by the system (10) (e.g., without the split), and the electronic signature of the rare flower is transmitted by a transmitter via a communication network using any known suitable signal transmission protocols (e.g., using WiFi or Bluetooth) to location B, where the scent database (15) can be accessed and managed (e.g., on a remote server). Thus, generally, location B may be identical or different from location A. The pattern of the electronic signature is then compared to the global scent database (15) resulting in, for example and without being limited, possible existing products or scents with the closest olfactive perception of that rare flower.

Functions of the system described hereinabove may be controlled through instructions executed by a computer-based control system which may be housed in the any one of the system modules. A control system suitable for use with embodiments described hereinabove may include, for example, and without being limiting, one or more processors connected to a communication bus, one or more volatile memories (e.g., random access memory—RAM) or non-volatile memories (e.g., Flash memory). A secondary memory (e.g., a hard disk drive, a removable storage drive, and/or removable memory chip such as an EPROM, PROM or Flash memory) may be used for storing data, computer programs or other instructions, to be loaded into the computer system.

For example, computer programs (e.g., computer control logic) may be loaded from the secondary memory into a main memory for execution by one or more processors of the control system. Alternatively or additionally, Computer programs may be received via a communication interface. Such computer programs, when executed, enable the computer system to perform certain features of the present invention as discussed herein. In particular, the computer programs, when executed, enable a control processor to perform and/or cause the performance of features of the present invention. Accordingly, such computer programs may implement controllers of the computer system.

In an embodiment where the invention is implemented using software, the software can be stored in a computer program product and loaded into the computer system using the removable storage drive, the memory chips or the communications interface. The control logic (software), when executed by a control processor, causes the control processor to perform certain functions of the invention as described herein.

In another embodiment, features of the invention are implemented primarily in hardware using, for example, hardware components such as application specific integrated circuits (ASICs) or field-programmable gated arrays (FP- GAs). Implementation of the hardware state machine so as to perform the functions described herein will be apparent to persons skilled in the relevant art(s). In yet another embodiment, features of the invention can be implemented using a combination of both hardware and software.

As described hereinabove and shown in the associated Figs., the present invention provides a system for evaluating scents and related methods. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

The invention claimed is:

1. A device for producing an odorant sample from an odorant material, said device comprising:
   a. a treatment cell for receiving said odorant material;
   b. a phase changing apparatus for applying a phase changing evaporation process to said odorant material therein in order to reach an equilibrium of at least of one of the following phases: liquid, solid, semi solid, emulsion, suspension, or aerosol, with a gaseous phase of said odorant material, thereby producing said odorant sample from said odorant material; and,
   c. an output for discharging said odorant sample from said treatment cell to a desired location.

2. The device of claim 1, wherein the phase changing apparatus comprises at least one of: a circulation pump, a diffuser, a surface area expanding device, a temperature regulator device, a flow regulating device, a humidifier, a desiccant, a pressure applying device, an absorbent cell, or a vaporization cell.

3. The device of claim 2, wherein the circulation pump is in communication with the treatment cell via an inlet and outlet circulation line for circulating the odorant material in the treatment cell, thereby increasing the gaseous concentration of the odorant material in the treatment cell.

4. The device of claim 2, further comprising an equilibrium sensor for measuring gaseous characteristics of the odorant material in the treatment cell.

5. The device of claim 4, further comprising a control unit for monitoring the measurements of the equilibrium sensor and managing the operation of the phase changing apparatus, wherein said phase changing apparatus activated while the odorant material is out of equilibrium, and deactivated once the odorant material reaches said equilibrium.

6. The device of claim 4, further comprising an output valve for regulating the discharge of the odorant sample from the treatment cell.

7. The device of claim 6, further comprising a scent sensor for regulating the discharge of the odorant sample from the treatment cell.

8. The device of claim 6, further comprising a control unit for monitoring the measurements of the equilibrium sensor and selectively regulating the closed state of the output valve while the odorant material is out of equilibrium, and an open state of the output valve once the odorant material reaches said equilibrium.

9. The device of claim 1, further comprising at least one output line through which the odorant sample flows upon being discharged from the treatment cell, and a flow sensor for measuring the flow rate of said odorant sample through said output line.

10. The device of claim 9, further comprising a sample dilution unit configured to controllably mix the odorant sample in a gas or a liquid.

11. The device of claim 9, further comprising a dilution-gas line for introducing dilution-gas into the output line, and a dilution-gas line control valve for regulating the flow of said dilution-gas into said output line.

12. The device of claim 11, further comprising a control unit for monitoring the measurements of the flow sensor and selectively switching the dilution-gas line control valve between a closed state and an open state, for changing characteristics of the odorant sample flowing through the output line.

13. A method of producing an odorant sample from an odorant material by applying a phase changing evaporation process to said odorant material in order to reach an equilibrium of at least of one of the following phases: liquid, solid, semi solid, emulsion, suspension and aerosol, with a gaseous phase of said odorant material, thereby producing said odorant sample from said odorant material, said method comprising the following steps:
   a. providing the device of claim 1;
   b. introducing said odorant material into said treatment cell;
   c. activating the phase changing apparatus;
   d. the equilibrium sensor measuring gaseous characteristics of the odorant material in the treatment cell;
   e. the control unit monitoring the measurements of the equilibrium sensor, and selectively maintaining the activation of the phase changing apparatus while said odorant material is out of the equilibrium, and deactivating said phase changing apparatus once said odorant material reaches said equilibrium;
   f. the control unit monitoring the measurements of the equilibrium sensor, and selectively switching the output valve between a closed state while the odorant material is out of the equilibrium, and an open state once the odorant material reaches said equilibrium; and
   g. discharging said odorant sample from said treatment cell to a desired location.

14. The method of claim 13, further comprising at least one of the following additional steps:
   a. when the odorant sample is discharged through the output into the output line, the flow sensor measures the flow rate of said odorant sample through the output line; or
   b. the control unit monitors the measurements of the flow sensor and regulates the closed and open states of the dilution-gas line control valve, for changing the characteristics of the odorant sample.

15. A system for analyzing and recording characterizing features of an odorant sample, said system comprising:
   a. a sampling module comprising the device of claim 1 for producing an odorant sample from an odorant material;
   b. an analyzing module for receiving and analyzing said odorant sample from said sampling module, wherein said analyzing module is comprised of a biological detector and an electronic detector, and wherein said analyzing module produces data associated with said odorant sample; and
   c. a database for storing said data therein.

16. The system of claim 14, wherein the analyzing module separates the flow of the odorant sample received from the sampling module, and directs one portion to the biological detector and another portion to the electronic detector.

17. The system of claim 14, wherein the analyzing module further comprises an odorant sample transfer medium on which to provide the odorant sample to the biological detector for analysis.

18. The system of claim 17, wherein the biological detector is associated with a living creature who provides analysis by relating at least one olfactive descriptor with the odorant sample to provide analysis of said odorant sample.

19. The system of claim 18, wherein the analysis further comprises generating at least one of:
 a. an olfactive rating provided by the living creature for the at least one olfactive descriptor, that is then related with the odorant sample;
 b. an olfactive index comprising at least two olfactive ratings; or
 c. a score that indicates the importance of the olfactive descriptors of the odorant sample for a predefined use.

20. The system of claim 19, wherein the electronic detector comprises at least one electronic sensor that analyzes and characterize the odorant sample, and generates an electronic signature that is then related with the odorant sample.

21. The system of claim 20, wherein the analyzing module further comprises a processing unit for generating a data record comprising the olfactive descriptor ratings and electronic signatures of each odorant sample, for storage in the database.

22. The system of claim 21, wherein the processing unit comprises a statistical data processing module that generates normalized olfactive descriptor data and normalized electronic signature data.

23. The system of claim 22, wherein the data record further comprises additional olfactive data generated from at least one of the biological detector and the electronic detector.

24. The system of claim 23, wherein the additional olfactive data comprises at least one of the following:
 a. machine olfactive descriptors;
 b. a normalized electronic signature;
 c. at least one olfactive index;
 d. at least one score indication;
 e. at least one olfactive descriptor;
 f. odorant sample identification;
 g. olfactive perception data; or
 h. sensorial properties.

25. The system of claim 21 wherein the processing unit further comprises a statistical data processing module to compare at least two odorant samples.

26. The system of claim 25, further comprising the following additional steps:
 a. generating a score of at least two odorant samples based on said odorant sample data record; and
 b. comparing at least two scores of at least two odorant samples.

27. A method of generating a database of odorant sample data records, said method comprising the steps of:
 a. providing the system according to claim 15 and producing said odorant sample from the odorant material;
 b. transferring said odorant sample to the biological detector and electronic detector for analysis;
 c. said biological detector analyzing said odorant sample and providing a rating based on olfactive descriptors related with said odorant sample, and said electronic detector analyzing said odorant sample and providing an electronic signature for said odorant sample;
 d. processing said rating from said biological detector and said electronic signature from said electronic detector, and generating an odorant sample data record; and,
 e. storing said odorant sample data record in a database.

28. A method of characterizing an odorant sample, said method comprising the steps of:
 a. generating a database of odorant sample records according to the method of claim 27;
 b. transferring an odorant sample to the electronic detector for analysis;
 c. said electronic detector analyzing said odorant sample and providing an electronic signature for said odorant sample;
 d. comparing said electronic signature of said odorant sample with electronic signatures from the odorant sample data records in the database; and,
 e. characterizing said odorant sample based on said comparison.

29. A method of calculating the change in olfactory sensitivity of an individual at a stage of onset of a health condition, said method comprising the steps of:
 a. generating a database according to claim 27;
 b. assembling individuals at various stages of onset of a predetermined health condition;
 c. obtaining at least one olfactive descriptor for at least one of the odorant samples in said database from the biological detector associated with each of said individuals, at each stage of onset of said health condition;
 d. correlating said obtained olfactive descriptors with a stage of onset of said health condition;
 e. optionally, creating a score from the said correlated olfactive descriptors;
 f. comparing at least one of: said obtained olfactive descriptors and said scores, with the respective olfactive descriptors and scores of said database generated according to claim 27; and,
 g. calculating the change in olfactory sensitivity for each stage of onset of said health condition.

30. The method of claim 29, further comprising diagnosing an individual who displays similar change in olfactory sensitivity, with a particular stage of onset of a predetermined health condition.

* * * * *